United States Patent [19]

Rohrbach et al.

[11] 4,218,363

[45] Aug. 19, 1980

[54] PREPARATION OF SUPPORT MATRICES FOR IMMOBILIZED ENZYMES

[75] Inventors: Ronald P. Rohrbach, Forest Lake; George W. Lester, Hoffman Estates, both of Ill.

[73] Assignee: UOP Inc., Des Plaines, Ill.

[21] Appl. No.: 951,947

[22] Filed: Oct. 16, 1978

[51] Int. Cl.² ............................................. C08K 9/00
[52] U.S. Cl. .................................. 260/42.14; 435/180; 260/42.43; 260/42.54; 525/344; 525/374; 525/384
[58] Field of Search ............... 526/31, 49, 55; 195/63; 260/42.14, 42.54, 42.43

[56] References Cited

U.S. PATENT DOCUMENTS

| | | | |
|---|---|---|---|
| 3,519,538 | 7/1970 | Messing et al. | 195/63 |
| 3,556,945 | 1/1971 | Messing et al. | 260/112.5 R |
| 3,650,900 | 3/1972 | Levin et al. | 195/63 |
| 3,654,003 | 4/1972 | Grossman | 264/139 |
| 3,705,084 | 12/1972 | Reynolds | 195/63 |
| 3,783,101 | 1/1974 | Tomb et al. | 195/63 |
| 3,796,634 | 3/1974 | Haynes et al. | 195/63 |
| 3,821,083 | 6/1974 | VanLeemputten et al. | 195/63 |

Primary Examiner—Melvyn I. Marquis
Attorney, Agent, or Firm—James R. Hoatson, Jr.; Raymond H. Nelson; William H. Page, II

[57] ABSTRACT

Support matrices for immobilized enzymes may be prepared by treating a solid porous, inorganic, water-insoluble support such as an alumina with a prepolymerized polymeric compound. After treating the solid support the resultant organic-inorganic composite may then be derivatized, one example of derivatization being nitration of the composite with nitric acid and reducing the nitro-substituted composite to form an aminopolystyrene alumina composite. This composite is then treated with a bifunctional monomer to form a copolymeric which is substantially entrapped in the pores of the solid support, said copolymeric material containing functionalized pendent groups to which an enzyme may be coupled to form an immobilized enzyme conjugate.

5 Claims, No Drawings

PREPARATION OF SUPPORT MATRICES FOR IMMOBILIZED ENZYMES

BACKGROUND OF THE INVENTION

It is known that enzymes, which are proteinaceous in nature and which are commonly water soluble, comprise biological catalysts which serve to regulate many and varied chemical reactions which occur in living organisms. The enzymes may also be isolated and used in analytical, medical and industrial applications. For example, they find use in industrial applications in the preparation of food products such as cheese or bread as well as being used in the preparation of alcoholic beverages. Some specific uses in industry may be found in the use of enzymes such as in the resolution of amino acids; in the modification of penicillin to form various substrates thereof; the use of various proteases in cheese making, meat tenderizing, detergent formulations, leather manufacture and as digestive aids; the use of carbohydrases in starch hydrolysis, sucrose inversion, glucose isomerization, etc.; the use of nucleases in flavor control; or the use of oxidases in oxidation prevention and in the color control of food products. These uses as well as many others have been well delineated in the literature.

As hereinbefore set forth, inasmuch as enzymes are commonly water soluble as well as being generally unstable and readily deactivated, they are also difficult either to remove from the solutions in which they are utilized for subsequent reuse or it is difficult to maintain their catalytic activity for a relatively extended period of time. The aforementioned difficulties will, of course, lead to an increase cost in the use of enzymes for commercial purposes due to the necessity for frequent replacement of the enzyme, this replacement being usually necessary with each application. To counteract the high cost of replacement, it has been suggested to immobilize or insolubilize the enzymes prior to the use thereof. By immobilizing the enzymes through various systems hereinafter set forth in greater detail, it is possible to stabilize the enzymes in a relative manner and, therefore, to permit the reuse of the enzyme which may otherwise undergo deactivation or be lost in the reaction medium. Such immobilized or insolubilized enzymes may be employed in various reactor systems such as in packed columns, stirred tank reactors, etc., depending upon the nature of the substrate which is utilized therein. In general, the immobilization of the enzymes provides a more favorable or broader environmental and structural stability, a minimum of effluent problems and materials handling as well as the possibility of upgrading the activity of the enzyme itself.

As hereinbefore set forth, several general methods, as well as many modifications thereof, have been described by which the immobilization of enzymes may be effected. One general method is to adsorb the enzyme at a solid surface as, for example, when an enzyme such as amino acid acylase is adsorbed on a cellulosic derivative such as DEAE-cellulose; papain or ribonuclease is adsorbed on porous glass; catalase is adsorbed on charcoal; trypsin is adsorbed on quartz glass or cellulose, chymotrypsin is adsorbed on kaolinite, etc. Another general method is to trap an enzyme in a gel lattice such as glucose oxidase, urease, papain, etc., being entrapped in a polyacrylamide gel; acetyl cholinesterase being entrapped in a starch gel or a silicon polymer; glutamic-pyruvic transaminase being entrapped in a polyamide or cellulose acetate gel, etc. A further general method is a cross-linking by means of bifunctional reagents and may be effected in combination with either of the aforementioned general methods of immobilization. When utilizing this method, bifunctional or polyfunctional reagents which may induce intermolecular cross-linking will covalently bind the enzymes to each other as well as on a solid support. This method may be exemplified by the use of glutaraldehyde or bisdiazobenzidine-2,2'-disulfonic acid to bind an enzyme such as papain on a solid support, etc. A still further method of immobilizing an enzyme comprises the method of a covalent binding in which enzymes such as glucoamylase, trypsin, papain, pronase, amylase, glucose oxidase, pepsin, rennin, fungal protease, lactase, etc., are immobilized by covalent attachment to a polymeric material which is attached by various means to an organic or inorganic solid porous support. This method may also be combined with the aforesaid immobilization procedures.

The above enumerated methods of immobilizing enzymes all possess some drawbacks which detract from their use in industrial processes: For example, when an enzyme is directly adsorbed on the surface of a support, the binding forces which result between the enzyme and the carrier support are often quite weak, although some prior art has indicated that relatively stable conjugates of this type have been obtained when the pore size of the support and the spin diameter of the enzyme are correlated. However, in such cases it is specified that the pore size of the support cannot exceed a diameter of about 1000 Angstroms. In view of this weak bond, the enzyme is often readily desorbed in the presence of solutions of the substrate being processed. In addition to this, the enzyme may be partially or extensively deactivated due to its lack of mobility or due to interaction between the support and the active site of the enzyme. Another process which may be employed is the entrapment of enzymes in gel lattices which can be effected by polymerizing an aqueous solution or emulsion containing the monomeric form of the polymer and the enzyme or by incorporating the enzyme into the preformed polymer by various techniques, often in the presence of a cross-linking agent. While this method of immobilizing enzymes has an advantage in that the reaction conditions utilized to effect the entrapment are usually mild so that often there is little alteration or deactivation of the enzyme, it also has disadvantages in that the conjugate has poor mechanical strength, which results in compacting when used in columns in continuous flow systems, which a concomitant plugging of the column. Such systems also have rather wise variations in pore size thus leading to some pore sizes which are large enough to permit the loss of enzyme. In addition, some pore sizes may be sufficiently small so that large diffusional barriers to the transport of the substrate and product will lead to reaction retardation, this being especially true when using a high molecular weight substrate. The disadvantages which are present when immobilizing an enzyme by intermolecular cross-linkage, as already noted, are due to the lack of mobility with resulting deactivation because of inability of the enzyme to assume the natural configuration necessary for maximum activity, particularly when the active site is involved in the binding process.

Covalent binding methods have found wide applications and may be used either as the sole immobilization technique or as an integral part of many of the methods already described in which cross-linking reactions are employed. This method is often used to bind the enzyme as well as the support through a bifunctional intermediary molecule in which the functional groups of the molecule, such as, for example, gamma-aminopropyltriethoxysilane, are capable of reacting with functional moieties present in both the enzyme and either an organic or inorganic porous support. A wide variety of reagents and supports has been employed in this manner and the method has the advantage of providing strong covalent bonds throughout the conjugate product as well as great activity in many cases. The covalent linkage of the enzyme to the carrier must be accomplished through functional groups on the enzyme which are non-essential for its catalytic activity such as free amino groups, carboxyl groups, hydroxyl groups, phenolic groups, sulfhydryl groups, etc. These functional groups will also react with a wide variety of other functional groups such as an aldehydo, isocyanato, acyl, diazo, azido, anhydro activated ester, etc., to produce covalent bonds. Nevertheless, this method also often has many disadvantages involving costly reactants and solvents, as well as specialized and costly porous supports and cumbersome multi-step procedures, which render the method of preparation uneconomical for commercial application.

The prior art is therefore replete with various methods for immobilizing enzymes which, however, in various ways fail to meet the requirements of economical industrial use. However, as will hereinafter be discussed in greater detail, none of the prior art compositions comprise the composition of matter of the present invention which constitutes an inorganic porous support containing a copolymer, formed in situ from a polyfunctional monomer, a low molecular weight polymer, a polymer hydrolysate, or a preformed polymer, of natural or synthetic origin by reaction with a bifunctional monomer, the copolymer which is formed being substantially entrapped within the pores of said support, and which contains terminally functionalized, pendent groups extending therefrom; the enzyme being covalently bound to the active moieties at the terminal reactive portions of the pendent groups, thus permitting the freedom of movement which will enable the enzyme to exercise maximum activity. A variable portion of the enzyme will also be adsorbed upon the matrix, but this will be recognized as an unavoidable consequence of almost all immobilization procedures involving porous inorganic supports and is not to be considered a crucial aspect of this invention. Furthermore, the bond between the inorganic support and the organic copolymer which has been prepared in situ in the pores of the support is not covalent but rather physico-chemical and mechanical in nature and the inorganic-organic matrix so produced presents high stability and resistance to disruption. As further examples of prior art, U.S. Pat. No. 3,566,945 relates to enzyme composites in which the enzyme is adsorbed directly to an inorganic carrier such as glass. U.S. Pat. No. 3,519,538 is concerned with enzyme composites in which the enzymes are chemically coupled by means of an intermediary silane coupling agent to an inorganic carrier. In similar fashion, U.S. Pat. No. 3,783,101 also utilizes an organosilane composite as a binding agent, the enzyme being covalently coupled to a glass carrier by means of an intermediate silane coupling agent, the silicon portion of the coupling agent being attached to the carrier while the organic portion of the coupling agent is coupled to the enzyme, the composition containing a metal oxide on the surface of the carrier disposed between the carrier and the silicon portion of the coupling agent. In U.S. Pat. No. 3,821,083 a water-insoluble polymer such as polyacrolein is deposited on an inorganic carrier and an enzyme is then covalently linked to the aldehyde groups of the polymer. However, according to most of the examples set forth in this patent, it is necessary to first hydrolyze the composite prior to the deposition of the enzyme on the polymer. Additionally the product which is obtained by the method of this patent suffers a number of disadvantages in that it first requires either the deposition, or initially the formation, of the desired polymer in an organic medium followed by its deposition on the inorganic carrier with a subsequent clean-up operation involving distillation to remove the organic medium. In addition to this, in another method set forth in this reference, an additional hydrolytic reaction is required in order to release the aldehyde groups from the initial acetal configuration in which they occurred in the polymer. Inasmuch as these aldehyde moieties are attached directly to the backbone of the polymer, the enzyme is also held adjacent to the surface of the polymer inasmuch as it is separated from the surface of the polymer by only one carbon atom of the reacting aldehyde group and, therefore, the enzyme is obviously subjected to the physico-chemical influences of the polymer as well as being relatively immobilized and inhibited from assuming its optimum configuration. Another prior art patent, namely, U.S. Pat. No. 3,705,084 discloses a macroporous enzyme reactor in which an enzyme is adsorbed on the polymeric surface of a macroporous reactor core and thereafter is cross-linked in place. By cross-linking the enzymes on the polymeric surface after adsorption thereof, the enzyme is further immobilized in part and cannot act freely as in its native state as a catalyst. The cross-linkage of enzymes in effect links them together, thereby preventing a free movement of the enzyme and decreases the mobility of the enzyme which is a necessary prerequisite for maximum activity.

U.S. Pat. No. 3,654,083 discloses a water-soluble enzyme conjugate which is prepared from an organic water-soluble support to which the enzyme is cross-linked and whose utility is limited only to cleaning compositions and pharmaceutical ointments. However, this enzyme composition also suffers from the disadvantages of the close proximity and interlocking of the enzyme and support, as well as the poor mechanical strength which is generally exhibited by enzyme conjugates based on organic polymeric supports.

U.S. Pat. No. 3,796,634 also discloses an immobilized biologically active enzyme which differs to a considerable degree from the immobilized enzyme conjugates of the present invention. The enzyme conjugate of this patent consists of an inorganic support comprising colloidal particles possessing a particle size of from 50 to 20,000 Angstroms with a polyethyleneimine, the latter being cross-linked with glutaraldehyde to staple the cross-linked polymer so formed as a monolayer on the surface of the colloidal particles, followed by adsorption of the enzyme directly onto this monolayer. Following this, the enzyme which is adsorbed as a monolayer on the surface of the colloidal particles is then cross-linked with additional glutaraldehyde to other adsorbed enzyme molecules to prevent them from being readily desorbed while in use. There is no indication of any covalent binding between enzyme and polymer matrix as is present in the present invention. By the enzyme molecules being cross-linked together on the surface of the support, this conjugate, therefore, is subjected to deactivation by both the cross-linking reaction and by the electronic and steric effects of the surface, said enzyme possessing limited mobility. Inasmuch as the product of this patent is colloidal in nature, it also possesses a very limited utility for scale-up to commercial operation, since it cannot be used in a continuous flow system such as a packed column because it would either be carried along and out of the system in the flowing liquid stream or, if a restraining membrane should be employed, the particles would soon become packed against the barrier to form an impervious layer. In addition, such a colloidal product could not readily be utilized in a fluidized bed apparatus, thereby limiting the chief utility to a batch type reactor such as a stirred tank type reactor from which it would have to be separated by centrifugation upon each use cycle. In contrast to this, the immobilized enzyme conjugates of the present invention may be employed in a wide variety of batch or continuous type reactors and therefore are much more versatile with regard to their modes of application.

In addition, another prior art reference U.S. Pat. No. 3,959,080 relates to a carrier matrix for immobilizing biochemical effective substances. However, the matrix which is produced according to this reference constitutes the product derived from the reaction of an organic polymer containing cross-linkable acid hydrazide or acid azide groups with a bifunctional cross-linking agent such as glutaraldehyde. However, this matrix also suffers from the relatively poor mechanical stability and other deficiencies which are characteristic of organic enzyme supports as well as the relatively complex organic reactions employed in preparing such polymeric hydrazides, etc.

This invention relates to a process for preparing support matrices for immobilized enzymes. More specifically, the invention is concerned with a process for preparing an organic-inorganic matrix which may be utilized as a support for immobilizing enzymes, said enzyme being covalently bound to functionalized pendent groups of an organic material at the terminal reactive portions thereof.

As hereinbefore set forth, the use of enzymes in analytical, medical or industrial applications may be greatly enhanced if said enzymes are in an immobilized condition, that is, said enzymes, by being in combination with other solid materials, are themselves in such a condition whereby they are not water soluble and therefore they may be subjected to repeated use in aqueous media while maintaining the catalytic activity of said enzyme. In order to be present in an immobilized state, the enzymes must be bound in some manner to a water insoluble carrier, thereby being commercially usable in an aqueous insoluble state.

It is therefore an object of this invention to provide a process for preparing combined organic-inorganic support matrices which are utilized as support materials for immobilizing an enzyme thereon.

A further object of this invention is to provide a process for preparing combined organic-inorganic matrices which are utilized as supports for covalently binding an enzyme to the functionalized pendent groups of said organic material at the reactive terminal portions thereof.

In one aspect an embodiment of this invention resides in a process for the preparation of an organic-inorganic matrix which comprises treating a solid porous, inorganic, water-insoluble support with a prepolymerized polymeric compound, derivatizing the resultant organic-inorganic composite, and recovering the desired organic-inorganic matrix.

A further embodiment of this invention is found in a process for the preparation of an organic-inorganic matrix which comprises treating gamma-alumina with polystyrene, nitrating the resultant polystyrene-alumina composite by treatment with fuming nitric acid at a temperature in the range of from about 0° to about 10° C., reducing the nitrated polystyrene-alumina composite by treatment with sodium dithionite at a temperature in the range of from about 100° to about 150° C., reacting the resultant aminopolystyrene-alumina composite with an excess of glutaraldehyde, and recovering the resultant organic-inorganic matrix.

Other objects and embodiments will be found in the following further detailed description of the present invention.

As hereinbefore set forth the present invention is concerned with a process for preparing support matrices for immobilized enzymes, said matrices comprising a combined organic-inorganic material. The inorganic material consists of a porous support material of the type hereinafter set forth in greater detail, said solid support material containing an organic material which is substantially entrapped in the pores of said organic supports. The organic material will contain pendent groups extending therefrom, said pendent groups containing terminally positioned functional moieties which will enable an enzyme to be covalently bound to said groups at the reactive terminal portions thereof. In contradistinction to other compositions of matter as set forth in the prior art, the support matrix of this invention may be prepared in a manner hereinafter set forth in greater detail utilizing relatively inexpensive reactants as well as utilizing more simple steps in the procedure for preparing said compositions. In addition, mechanical strength and stability of enzyme conjugates which result from the covalent binding of enzymes to the support matrices will be greater than that which is possessed by the immobilized enzymes of the prior art. Therefore, it will be readily apparent that the compositions of matter which are prepared according to the process of the present invention possess economical advantages which are useful for industrial applications.

Examples of inorganic supports which may be utilized as one component of the support matrices of the present invention will consist of a wide variety of materials including porous supports such as alumina which possess pore diameters ranging from about 100 Angstroms up to about 55,000 Angstroms and which also possess an Apparent Bulk Density (ABD) in the range of from about 0.1 to about 0.6. The surface area of the particular inorganic porous support will also vary over a relatively wide range, said range being from about 1 to about 500 m$^2$/gm, the preferred range of surface area being from about 5 to about 400 m$^2$/gm. The configuration of the inorganic porous support material will vary, depending upon the particular type of support which is utilized. For example, the support material may be in spherical form, particulate form ranging from fine particles to macrospheres, as a ceramic monolith which may or may not be coated with a porous inorganic oxide, a membrane, ceramic fibers, alone or woven into a cloth, silica, mixtures of metallic oxides, sand particles, zeolites, mica, etc. The particle size may also vary over a wide range, again depending upon the particular type of support which is employed and also upon the substrate and the type of installation in which the enzyme conjugate is to be used. For example, if the support is in spherical form, the spheres may range in size from about 0.01" to about 0.25" in diameter, the preferred size ranging from about 1/32" to ⅛" in diameter. When the support is in particulate form, the particle size may also range between about the same limits. In terms of U.S. standard mesh sizes, such particles may range from about 2.5 to about 100 mesh, with about 10–40 mesh sizes preferred. Likewise, if the support is in the shape of ceramic fibers, the fibers may range from about 0.5 to about 20 microns in diameter or, if in the form of a membrane, the membrane may comprise a ceramic material which is cast into a thin sheet. It is to be understood that the aforementioned types of support configuration and size of the various supports are given merely for purposes of illustration, and it is not intended that the present invention be necessarily limited thereto.

It is also contemplated that the porous support materials may be coated with various oxides of the type hereinbefore set forth or consist of mixtures thereof, or may have incorporated therein various other inorganic materials such as boron phosphate, etc., these inorganic materials imparting special properties to the support material. A particularly useful form of support will constitute a ceramic body which may have the type of porosity herein described for materials of the present invention or it may be honeycombed with connecting macro size channels throughout, such materials being commonly known as monoliths, and which may be coated with various types of porous alumina, zirconia, titanium oxide, etc. The use of such a type of support has the particular advantage of permitting the free flow of highly viscous substrates which are often encountered in commercial enzyme catalyzed reactions.

One component of the organic portion of the support matrix comprises an aminopolystyrene while the other component of the organic portion comprises a bifunctional monomer. The bifunctional monomer reactant is present in sufficient excess as needed to produce pendent terminally functionalized groups, said bifunctional monomer being present in a range of from about 2 to about 50 moles or more relative to the reactive moieties of the support composite, the preferred range being from about 4 to about 25 moles of excess.

The functional groups which are present on the bifunctional monomer will comprise well-known reactive moieties capable of binding readily with amino groups such as acyl, isocyanato, carbonyl, etc., moieties. As was also hereinbefore set forth, the reactive groups of the bifunctional compounds are preferably, but not necessarily, separated by chains containing from about 4 to about 10 carbon atoms. The reactive moieties of the bifunctional compounds are therefore capable of covalently bonding with both the aminopolystyrene component of the support matrix and subsequently, after washing out unreacted materials, also with the amino groups of the enzyme which is to be added in a subsequent step, said enzyme being then covalently bound to the reactive functional group at the terminal portion of the pendent chain. After addition of the enzyme to this composition, a relatively stable enzyme conjugate will be produced which possesses high activity and high stability. The unreacted enzyme can also be recovered for reuse. Due to the large excess of intermediate, or spacer, bifunctional monomeric molecules which are used, the matrix will contain pendent groups comprising the spacer molecules, said molecules extending from the matrix and having reactive moieties available at the terminal portions thereof which are capable of reacting with and binding the enzyme to the aforesaid spacer molecules via covalent bonds. Therefore, it is readily apparent that a suitable organic-inorganic matrix which is applicable in binding enzymes in many situations will be formed, provided that a large enough excess of the bifunctional molecule is used to provide reactive pendent groups which are capable of subsequently reacting with the enzyme to be immobilized. By utilizing these functional pendent groups as a binding site for the enzymes, it will permit the enzymes to have a greater mobility and thus permit the catalytic activity of the enzyme to remain at a high level for a relatively longer period of time than will be attained when the enzyme has been immobilized by any of the other methods such as entrapment in a gel lattice, adsorption on a solid surface or cross-linkage of the enzyme with adjacent enzyme molecules by means of bifunctional reagents, etc. Not all formulations, however, will produce equivalent results in terms of stability or activity.

Examples of enzymes which may be immobilized by a covalent bonding reaction and which contain an amino group capable of reacting with an aldehydic, isocyanato, acyl, etc., moiety of the pendent group which is attached to a polymeric material substantially entrapped in the pores of a porous support material will include trypsin, papain, hexokinase, betagalactosidase (lactase), ficin, bromelain, lactate dehydrogenase, glucoamylase, chymotrypsin, pronase, glucose isomerase, acylase, invertase, amylase, glucose oxidase, pepsin, rennin, protease, xylanase, cellulase, etc. In general any enzyme whose active site is not involved in the covalent bonding can be used although not necessarily with equivalent results. While the aforementioned discussion was centered about pendent groups which contain as a functional moiety thereon an aldehydic or isocyanato group, it is also contemplated within the scope of this invention that the pendent group can contain other functional moieties capable of reaction with carboxyl, sulfhydryl or other moieties usually present in enzymes. However, the covalent bonding of enzymes containing these other moieties with other pendent groups may not necessarily be effected with equivalent results and may also involve appreciably greater costs in preparing intermediates. It is to be understood that the aforementioned listing of porous solid supports, monomers, hydrolysates, polymers and enzymes are only representative of the various classes of compounds which may be used, and that the present invention is not necessarily limited thereto.

The process of this invkention may be effected in a batch type operation. In the preferred method of preparation a solid support of the type hereinbefore set forth in greater detail is treated with a solution of a prepolymerized polymeric compound, said polymeric compound being solubilized in an appropriate solvent such as methyl ether, ethyl ether, propyl ether, isopropyl ether, methyl alcohol, ethyl alcohol, propyl alcohol, isopropyl alcohol, cyclopentane, cyclohexane, methylcyclopentane, benzene, toluene, xylenes, acetone, etc. After allowing the contact of the polymeric compound with the support for a predetermined period of time, the solvent may be removed by decantation, evaporation, or any other method known in the art whereby the polymeric compound will deposit as a thin film of polymer onto the surface of the solid support. Examples of polymeric compounds which may be employed will include polystyrene, or substituted polystyrene such as nitropolystyrene, etc. Following the deposition of the polymeric compound on the surface of the support, the composite may then be derivatized to the functional group of interest. For example, in the event that the polymeric compound comprises polystyrene, the polystyrene-solid support composite may then be nitrated by adding the composite to a nitrated agent such as nitric acid and preferably 90% fuming nitric acid. The addition of the composite to the acid is effected at a relatively slow rate while maintaining the nitric acid preferably at subambient temperatures ranging from about 0° to about 10° C. by means of external cooling means such as an ice bath, cooling coils, etc. However, such low temperatures are not critical to the success of the nitration reaction and higher temperatures may be employed if so desired. The nitration of the polystyrenesolid support composite is allowed to proceed for a period of time which may range from about 1 to about 4 hours or more, following which the nitrated composite is recovered, washed with water and a solvent.

The nitrated composite may then be reduced by adding said composite to an aqueous solution containing a reducing agent such as sodium dithionite, following which the solution is added to the boiling point and maintained thereat for a period of time which may range from about 0.5 to about 2 hours or more. At the end of this period of time, the aminopolystyrene-solid support composite is recovered, washed, dried under vacuum and maintained preferably under a nitrogen blanket.

Alternatively, if the polymerized compound comprises nitropolystyrene, the desired product may be obtained by undergoing only the latter step of the derivatization process, that is, the reduction of the nitropolystyrene to form aminopolystyrene, the latter containing the functional group of interest.

In another embodiment of the process, the deposition of the prepolymerized polymeric compound on the surface of the substrate or solid support may be effected by dissolving the polymeric compound in a suitable solvent of the type hereinbefore set forth and precipitating out the polymer on the surface of the substrate by the addition of a second solvent such as water in which the polymer is insoluble.

To prepare the desired support matrix which will contain pendent groups to which an enzyme may be immobilized, the organic-inorganic composite, an example of which being an aminopolystyrene-alumina composite, is then contacted with a sufficiently large excess of a bifunctional monomer, said excess being in the range of from about 3 to about 50 or more mole proportions relative to the amino groups of the aminopolystyrene which will react therewith to provide pendent groups extending from the resulting copolymer which contains unreacted terminal functional moieties. The reactive groups of the bifunctional monomer are preferably separated by a chain containing from about 4 to about 10 carbon atoms, which also may be cyclic as well as a straight chain. This bifunctional monomer is added preferably in an aqueous solution whereby the copolymer which is formed will be substantially entrapped in the pores of the inorganic support. The pendent groups so produced will contain unreacted terminal functional moieties due to the fact that a sufficient excess amount of the bifunctional monomer is employed in treating the aminopolystyrene composite support. The unreacted functional moieties are then available for covalent binding to the enzyme, which is added to the resulting organic-inorganic matrix, again usually in an aqueous solution. Prior to treatment with the enzyme, the support matrix is thoroughly washed with distilled water to remove any unreacted bifunctional monomer. The treatment of the support matrix with the aqueous solution of the enzyme will result in the enzyme being covalently bound to the pendent functionalized groups at the terminal portions thereof. It is therefore readily apparent that the entire immobilization procedure can be conducted in a simple and inexpensive manner, for example, in a column packed with inorganic supports utilizing an aqueous or inexpensive solvent media procedure being conducted over a temperature differential which may range from subambient (about 0° C.) up to relatively elevated temperatures of about 100° C., said procedure being effected by utilizing a minimum of operating steps and, in addition, permitting a ready recovery of the excess reactants, unbound enzyme, and finished compositions of matter from which the excess reactant and unbound enzyme may be removed.

It is also contemplated within the scope of this invention that the formation of the finished composition of matter may also be effected in a continuous manner of operation. When such a type of operation is used, a quantity of the solid support is placed in an appropriate apparatus which may, if so desired, constitute a column. The solid support material, as in the case of the batch type operation, may be in any form desired such as powder, pellets, monoliths, beads, etc., and is charged to the column. Following this a solution of the prepolymerized polymeric compound is passed over the support for a predetermined period of time following which the solvent is removed by evaporation. The polymeric compound-solid support composite is then washed with water, and subjected to a derivatization process such as by treatment with fuming nitric acid at subambient temperatures and reduction at an elevated temperature to form the desired functional group of interest. After forming the desired functional group, the support composite is washed and treated with an excess of a bifunctional monomer also preferably in aqueous solution, said bifunctional monomer being continuously charged to the column at a rate which is sufficient to provide the excess of said monomer. Upon completion of the desired residence time, the unreacted excess monomer is removed by draining and thereafter the organic-inorganic matrix is thoroughly washed with water to remove any water soluble and unreacted materials.

To thereafter form an immobilized enzyme conjugate an aqueous solution of an enzyme of the type hereinbefore set forth in greater detail is contacted or recycled to the column whereby a covalent bonding of the enzyme to the terminal groups of the functionalized pendent moieties which extend from the matrix is effected. This occurs until there is no further covalent binding of the enzyme to the pendent moieties. The excess enzyme is recovered in the effluent after draining and washing the column, the column thus being ready for use in chemical reactions in which the catalytic effect of the enzyme is to take place. While these procedures are, for the most part, conducted within the time, temperature and concentration parameters hereinbefore described in the batch type procedure and which result in comparable immobilized enzyme complexes, it is also contemplated within the scope of this invention that with suitable modifications of pH, temperature and time parameters which may be obvious to those skilled in the art, the process may be applied to a wide variety of inorganic supports, polymer forming reactants and enzymes.

The following examples are given for purposes of illustrating the process of the present invention. However, it is to be understood that these examples are given merely for purposes of illustration and that the present invention is not necessarily limited thereto.

EXAMPLE I

In this example, 1 gram of alumina beads, having an apparent bulk density (ABD) of 0.344 and pore sizes ranging from 200 Angstroms to 10,000 Angstroms, which were 1/16" in diameter were treated with a solution with 5 ml of a solution comprising prepolymerized polystyrene dissolved in acetone. The beads were allowed to adsorb in this solution under vacuum for a period of 1 hour following which the liquid was evaporated, the beads were washed with water and the polystyrene-alumina support was slowly added to 50 ml of 90% fuming nitric acid. The addition of the support to the acid was effected at a temperature of 0° C., the temperature being maintained by placing the apparatus in an ice bath. After a period of 2 hours the nitrated support was removed, washed with water and acetone. Thereafter the composite along with 1 gram of sodium dithionite was added to 100 ml of distilled water. The mixture was heated to boiling and maintained at this temperature for 1 hour following which the aminopolystyrene-alumina support was washed with distilled water, dried under vacuum and maintained under a nitrogen atmosphere.

The experiment which was prepared accormding to the above paragraph was mixed with 10 ml of a 25% aqueous solution of glutaraldehyde which had a pH of 1.4, the mixing being permitted to proceed for a period of 1 hour at room temperature. At the end of the 1 hour period, the excess glutaraldehyde was decanted and the organic-inorganic support matrix was washed with water several times in order to effectively remove unreacted and unadsorbed reagents. The final immobilized enzyme conjugate was then prepared by treating the matrix with 1000 units/gram of glucose isomerase, said immobilization of the enzyme being effected during a period of 16 hours while maintaining the composite at 4° C. by means of an ice bath. At the end of the 16 hour period the residual and unbound enzyme was washed with water and a sodium chloride solution.

The immobilized enzyme composite was then packed in a column and a 45% weight by volume solution of fructose with $5 \times 10^{-3}$ M $MgCl_2$ was passed over the beads while maintaining the temperature at 60° C. for a period of 2 hours. At the end of the 2 hour period the amount of glucose formed and the flow rate were assayed. It was found that the activity of the enzyme was 227 units/gram at a flow rate of 2 ml/min.; the term "unit" being defined as the grams of glucose formed per hour per gram of immobilized enzyme conjugate. In addition, it was found that the coupling efficiency of the conjugate was 54%.

When the above experiment was repeated with the exception that the alumina substrate had an ABD of 0.2 instead of 0.344, all other parameters of the experiment being identical, it was found that the activity of the conjugate assayed out to 263 units/gram at a flow rate of 2 ml/min. with a coupling efficiency of 43%.

EXAMPLE II

In this example, 1 gram of an alumina base which had an ABD of 0.20 was treated with a 5% solution of prepolymerized nitropolystyrene dissolved in dimethylformimide. The base was emersed in this solution for a period of 1 hour following which the excess solution was removed and the solvent removed by evaporation. After washing the composite with water, it was then placed in 100 ml of distilled water along with 1 gram of sodium dithionite and the mixture was boiled for a period of 1 hour. At the end of this time the beads were washed with distilled water, dried under vacuum, and maintained under a nitrogen atmosphere. The aminopolystyrene-alumina composite was then treated with 10 ml of a 25% aqueous glutaraldehyde solution which had a pH of 3.5. After allowing the reaction to proceed for a period of 1 hour at room temperature, the excess glutaraldehyde was decanted, the matrix was washed several times with water and treated with 1000 units of glucose isomerase. The coupling of the glucose isomerase to the support matrix was effected at a temperature of 4° C. for a period of 16 hours. The resulting immobilized glucose isomerase conjugate was thoroughly washed with water and a 2 M aqueous sodium chloride solution to remove any undissolved enzyme.

The thus formed immobilized enzyme conjugate was packed in a suitable column and a 45% solution of fructose with $5 \times 10^{-3}$ M $MgCl_2$ was passed over the conjugate while maintaining the temperature at 60° C. for a period of 2 hours. At the end of the 2 hour period the amount of glucose formed and the flow rate were assayed. It was found that the activity of the enzyme was 131 units/gram.

We claim as our invention:

1. A process for the preparation of an organic-inorganic support matrix having pendent bonding sites for enzymatic conjugates which comprises:
   (a) adsorbing on a solid, porous, inorganic, water-insoluble support a nitropolystyrene compound;
   (b) chemically reducing said nitropolystyrene compound and solid, porous, inorganic, water-insoluble support of step (a) with a chemical reducing agent to form aminopolystyrene;
   (c) contacting with said reduced aminopolystyrene adsorbed support of step (b) a bifunctional monomer comprising an organic compound containing a moiety selected from the group consisting of acyl, isocyanato and carbonyl moieties in molar excess of from about 3 to about 50 mole proportions of bifunctional monomer relative to the amino of the aminopolystyrene compound formed in step (b); and
   (d) recovering said organic-inorganic support matrix having pendent bonding sites for enzymatic conjugate attachment thereto.

2. The process as set forth in claim 1 in which said solid support compirses a metallic oxide.

3. The process as set forth in claim 2 in which said metallic oxide in an alumina.

4. The process as set forth in claim 3 in which said alumina is gamma-alumina.

5. The process as set forth in claim 1 in which said solid support is a porous silica.

* * * * *